(12) United States Patent
Ranu

(10) Patent No.: US 9,643,010 B2
(45) Date of Patent: May 9, 2017

(54) METHODS AND SYSTEMS FOR EMPLOYING A DUTY CYCLE IN ELECTRICAL STIMULATION OF PATIENT TISSUE

(71) Applicant: BOSTON SCIENTIFIC NEUROMODULATION CORPORATION, Valencia, CA (US)

(72) Inventor: Emarit A. S. Ranu, Fort Collins, CO (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/572,606

(22) Filed: Dec. 16, 2014

(65) Prior Publication Data
US 2015/0174411 A1   Jun. 25, 2015

Related U.S. Application Data

(60) Provisional application No. 61/918,219, filed on Dec. 19, 2013.

(51) Int. Cl.
*A61N 1/36* (2006.01)
*A61N 1/02* (2006.01)
*A61N 1/05* (2006.01)

(52) U.S. Cl.
CPC ......... *A61N 1/36175* (2013.01); *A61N 1/025* (2013.01); *A61N 1/3615* (2013.01); *A61N 1/0553* (2013.01); *A61N 1/36* (2013.01)

(58) Field of Classification Search
CPC .................. A61N 1/36175; A61N 1/3615
See application file for complete search history.

(56) References Cited

U.S. PATENT DOCUMENTS

| | | | |
|---|---|---|---|
| 6,051,017 A | 4/2000 | Loeb et al. | |
| 6,181,969 B1 | 1/2001 | Gord | |
| 6,516,227 B1 | 2/2003 | Meadows et al. | |
| 6,609,029 B1 | 8/2003 | Mann et al. | |

(Continued)

FOREIGN PATENT DOCUMENTS

WO   2012/148401 A1   11/2012

OTHER PUBLICATIONS

International Search Report and Written Opinion for PCT/US2014/070668 mailed Feb. 12, 2015.

*Primary Examiner* — Joseph Dietrich
(74) *Attorney, Agent, or Firm* — Lowe Graham Jones PLLC; Bruce E. Black

(57) ABSTRACT

A method of delivering electrical stimulation energy includes receiving stimulation parameters such as a selection of one or more electrodes, a stimulation amplitude, and a stimulation frequency. The stimulation parameters define, at least in part, an electrical stimulation energy deliverable as a series of electrical pulses at the stimulation frequency. The method also includes receiving a duty cycle parameter that indicates a relative number of the electrical pulses to be suppressed; and delivering the electrical stimulation energy to patient tissue through the stimulation lead. A percentage of the electrical pulses are suppressed according to the duty cycle parameter. Optionally, a distribution parameter is received that indicates how suppressed electrical pulses are to be distributed among the electrical pulses. Optionally, a suppression level parameter is received that indicates a reduction of the stimulation amplitude for each electrical pulse that is to be suppressed.

20 Claims, 8 Drawing Sheets

(56) References Cited

U.S. PATENT DOCUMENTS

| | | |
|---|---|---|
| 6,609,032 B1 | 8/2003 | Woods et al. |
| 6,741,892 B1 | 5/2004 | Meadows et al. |
| 7,203,548 B2 | 4/2007 | Whitehurst et al. |
| 7,244,150 B1 | 7/2007 | Brase et al. |
| 7,330,756 B2 | 2/2008 | Marnfeldt |
| 7,437,193 B2 | 10/2008 | Parramon et al. |
| 7,444,180 B2 | 10/2008 | Kuzma et al. |
| 7,672,734 B2 | 3/2010 | Anderson et al. |
| 7,702,385 B2 | 4/2010 | Moffitt et al. |
| 7,706,892 B2 | 4/2010 | Colvin et al. |
| 7,761,165 B1 | 7/2010 | He et al. |
| 7,860,570 B2 | 12/2010 | Whitehurst et al. |
| 7,949,395 B2 | 5/2011 | Kuzma |
| 7,957,805 B2 | 6/2011 | He |
| 7,974,706 B2 | 7/2011 | Moffitt et al. |
| 8,165,696 B2 | 4/2012 | McClure et al. |
| 8,175,710 B2 | 5/2012 | He |
| 8,224,450 B2 | 7/2012 | Brase |
| 8,364,278 B2 | 1/2013 | Pianca et al. |
| 2004/0210271 A1 | 10/2004 | Campen et al. |
| 2005/0222646 A1 | 10/2005 | Kroll et al. |
| 2007/0150036 A1 | 6/2007 | Anderson |
| 2008/0177338 A1 | 7/2008 | Ben-David et al. |

METHODS AND SYSTEMS FOR EMPLOYING A DUTY CYCLE IN ELECTRICAL STIMULATION OF PATIENT TISSUE

CROSS-REFERENCE TO RELATED APPLICATIONS

This application claims the benefit under 35 U.S.C. §119(e) of U.S. Provisional Patent Application Ser. No. 61/918,219, filed Dec. 19, 2013, which is incorporated herein by reference.

FIELD

The present invention is directed to the area of implantable electrical stimulation systems and methods of making and using the systems. The present invention is also directed to implantable electrical stimulation systems employing a duty cycle, as well as methods of making and using the electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is a non-transitory computer-readable storage medium having processor-executable instructions for delivering electrical stimulation energy through at least one electrode of an implantable electrical stimulation system. The processor-executable instructions when installed onto a system enable the system to perform actions. The actions include receiving stimulation parameters such as a selection of one or more electrodes, a stimulation amplitude, and a stimulation frequency. The stimulation parameters define, at least in part, an electrical stimulation energy deliverable as a series of electrical pulses at the stimulation frequency. The actions also include receiving a duty cycle parameter that indicates a relative number of the electrical pulses to be suppressed; and delivering the electrical stimulation energy to patient tissue through the one or more electrodes. A percentage of the electrical pulses are suppressed according to the duty cycle parameter.

Another embodiment is a method of delivering electrical stimulation energy using an implantable electrical stimulation system. The method includes receiving stimulation parameters such as a selection of one or more electrodes, a stimulation amplitude, and a stimulation frequency. The stimulation parameters define, at least in part, an electrical stimulation energy deliverable as a series of electrical pulses at the stimulation frequency. The method also includes receiving a duty cycle parameter that indicates a relative number of the electrical pulses to be suppressed; and delivering the electrical stimulation energy to patient tissue through the one or more electrodes. A percentage of the electrical pulses are suppressed according to the duty cycle parameter.

Yet another embodiment is an electrical stimulation system including an electrical stimulation lead comprising multiple electrodes; a control module coupleable to the electrical stimulation lead; and a processor in communication with the control module for executing processor-readable instructions that enable actions. The actions include receiving stimulation parameters such as a selection of one or more electrodes of a stimulation lead, a stimulation amplitude, and a stimulation frequency. The stimulation parameters define, at least in part, an electrical stimulation energy deliverable as a series of electrical pulses at the stimulation frequency. The actions also include receiving a duty cycle parameter that indicates a relative number of the electrical pulses to be suppressed; and delivering the electrical stimulation energy to patient tissue through the stimulation lead. A percentage of the electrical pulses are suppressed according to the duty cycle parameter.

Any of the embodiments described above can optionally include receiving a distribution parameter that indicates how suppressed electrical pulses are to be distributed among the electrical pulses.

Any of the embodiments described above can optionally include receiving a suppression level parameter that indicates a reduction of the stimulation amplitude for each electrical pulse that is to be suppressed according to the duty cycle parameter.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation systems employing a duty cycle, as well as methods of making and using the electrical stimulation systems.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Application Publication No. 2007/0150036, all of which are incorporated by reference. The methods and systems described herein can also be utilized for electrical stimulation systems that take the form of an implantable microstimulator. Examples of suitable implantable microstimulators include, but are not limited to, those described in U.S. Pat. Nos. 6,051,017; 6,609,032; 7,203,548; 7,330,756; 7,437,193; 7,444,180; 7,702,385; 7,706,892; 7,860,570; 7,957,805; 8,165,696; and 8,175,710, all of which are incorporated by reference.

Figure 1:
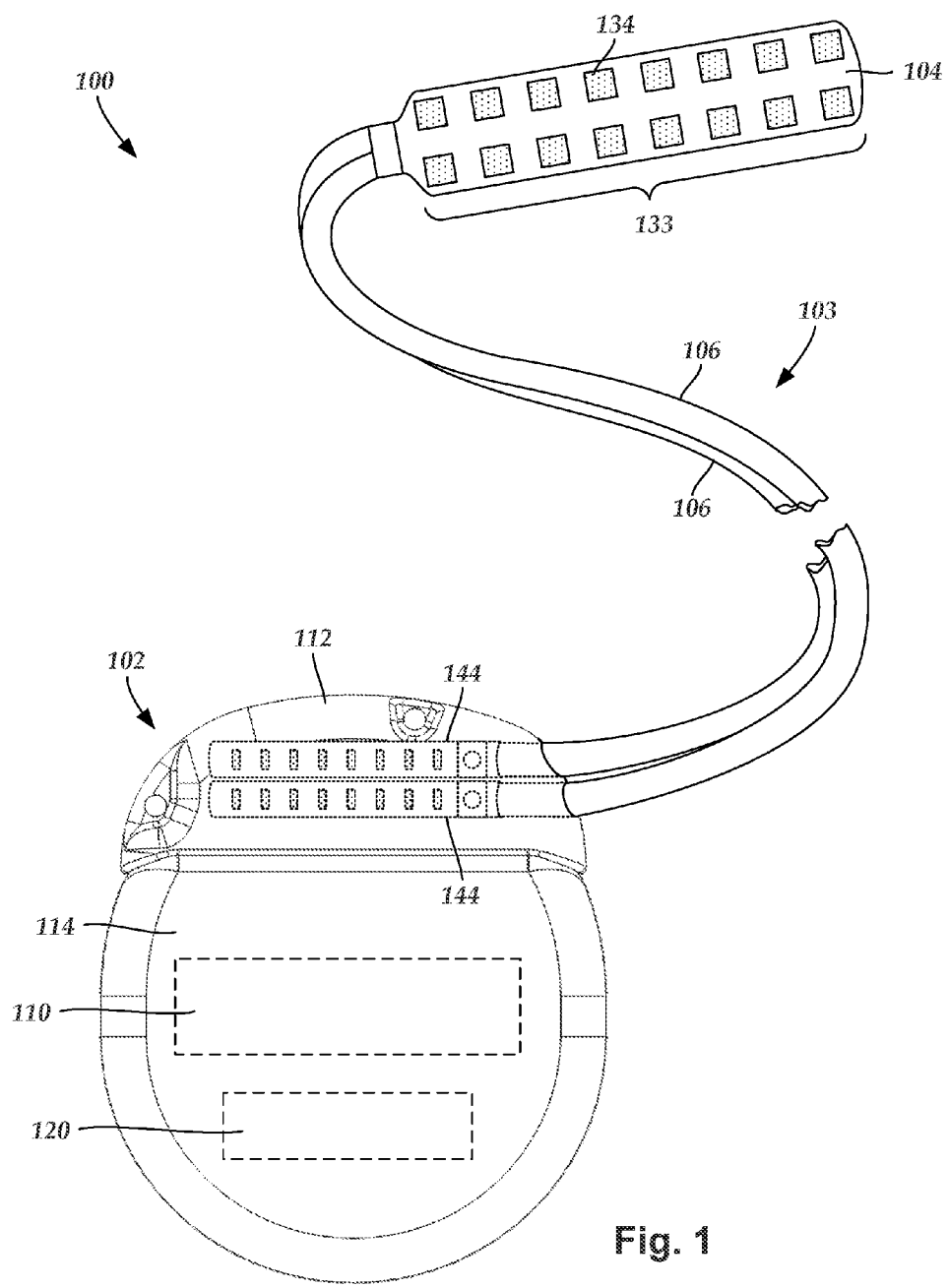
FIG. 1 is a schematic view of one embodiment of an electrical stimulation system that includes a paddle lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes a paddle body 104 and one or more lead bodies 106. In FIG. 1, the lead 103 is shown having two lead bodies 106. It will be understood that the lead 103 can include any suitable number of lead bodies including, for example, one, two, three, four, five, six, seven, eight or more lead bodies 106. An array 133 of electrodes, such as electrode 134, is disposed on the paddle body 104, and an array of terminals (e.g., 310 in FIG. 3A-3B) is disposed along each of the one or more lead bodies 106.

It will be understood that the electrical stimulation system can include more, fewer, or different components and can have a variety of different configurations including those configurations disclosed in the electrical stimulation system references cited herein. For example, instead of a paddle body, the electrodes can be disposed in an array at or near the distal end of a lead body forming a percutaneous lead. As another example, a paddle lead can include a paddle body with a single electrode or a percutaneous lead can include a single electrode. In some embodiments, the control module may also include an electrode.

Figure 2:
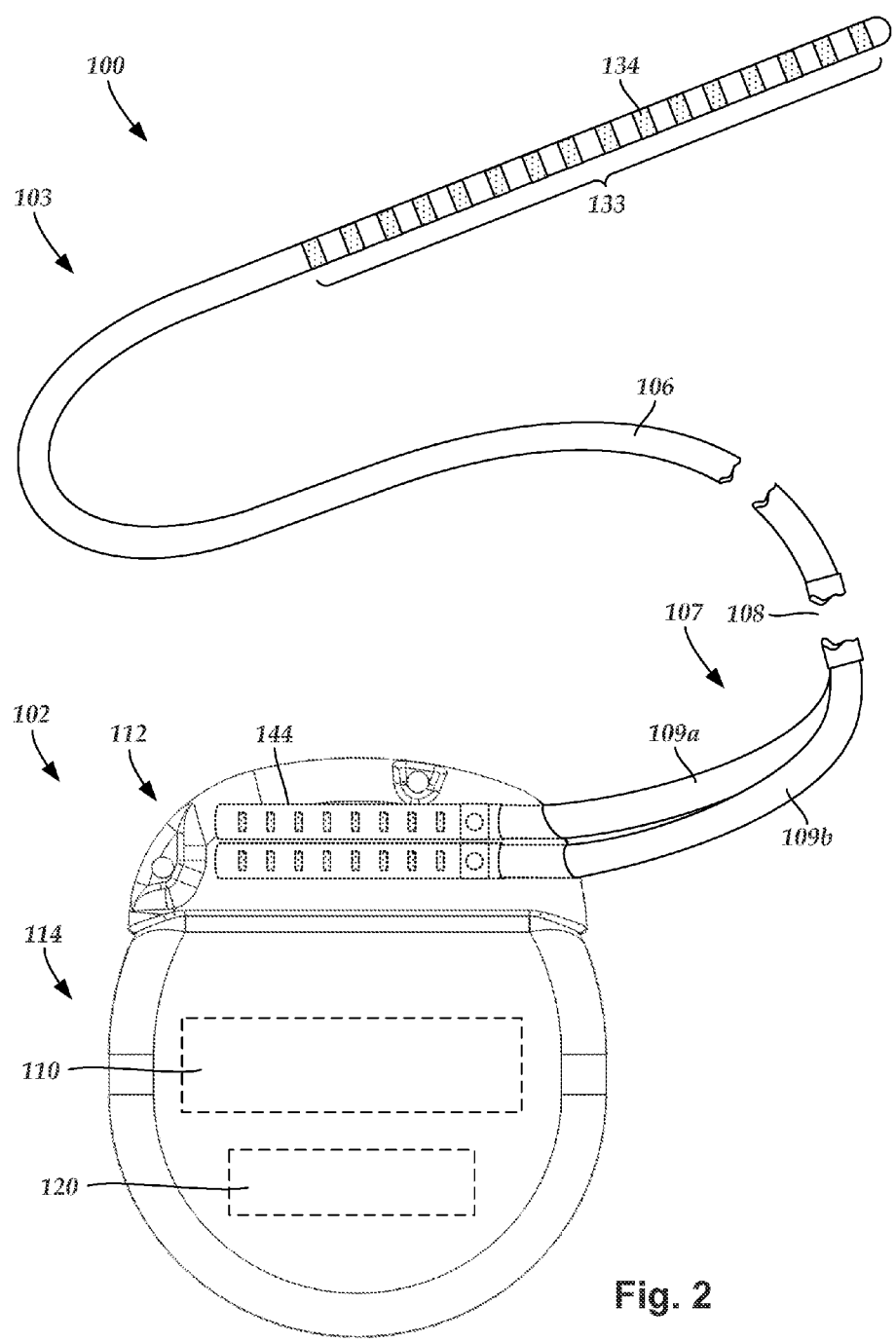
FIG. 2 is a schematic view of one embodiment of an electrical stimulation system that includes a percutaneous lead electrically coupled to a control module, according to the invention.

FIG. 2 illustrates schematically another embodiment of the electrical stimulation system 100, where the lead 103 is a percutaneous lead. In FIG. 2, the electrodes 134 are shown disposed along the one or more lead bodies 106. In at least some embodiments, the lead 103 is isodiametric along a longitudinal length of the lead body 106.

The lead 103 can be coupled to the control module 102 in any suitable manner. In FIG. 1, the lead 103 is shown coupling directly to the control module 102. In at least some other embodiments, the lead 103 couples to the control module 102 via one or more intermediate devices (324 in FIG. 3B). For example, in at least some embodiments one or more lead extensions 324 (see e.g., FIG. 3B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 2, the electrical stimulation system 100 is shown having a splitter 207 configured and arranged for facilitating coupling of the lead 103 to the control module 102. The splitter 107 includes a splitter connector 108 configured to couple to a proximal end of the lead 103, and one or more splitter tails 109a and 109b configured and arranged to couple to the control module 102 (or another splitter, a lead extension, an adaptor, or the like).

With reference to FIGS. 1 and 2, the control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including the paddle body 104, the one or more of the lead bodies 106, and the control module 102, are typically implanted into the body of a patient. The electrical stimulation system can be used for a variety of applications including, but not limited to deep brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium.

Any suitable number of electrodes 134 can be disposed on the lead including, for example, one, two, three, four, five, six, seven, eight, nine, ten, eleven, twelve, fourteen, sixteen, twenty-four, thirty-two, or more electrodes 134. In the case of paddle leads, the electrodes 134 can be disposed on the paddle body 104 in any suitable arrangement. In FIG. 1, the electrodes 134 are arranged into two columns, where each column has eight electrodes 134.

The electrodes of the paddle body 104 (or one or more lead bodies 106) are typically disposed in, or separated by, a non-conductive, biocompatible material such as, for example, silicone, polyurethane, polyetheretherketone ("PEEK"), epoxy, and the like or combinations thereof. The one or more lead bodies 106 and, if applicable, the paddle body 104 may be formed in the desired shape by any process including, for example, molding (including injection molding), casting, and the like. The non-conductive material typically extends from the distal ends of the one or more lead bodies 106 to the proximal end of each of the one or more lead bodies 106.

In the case of paddle leads, the non-conductive material typically extends from the paddle body 104 to the proximal end of each of the one or more lead bodies 106. Additionally, the non-conductive, biocompatible material of the paddle body 104 and the one or more lead bodies 106 may be the same or different. Moreover, the paddle body 104 and the one or more lead bodies 106 may be a unitary structure or can be formed as two separate structures that are permanently or detachably coupled together.

Figure 3A:
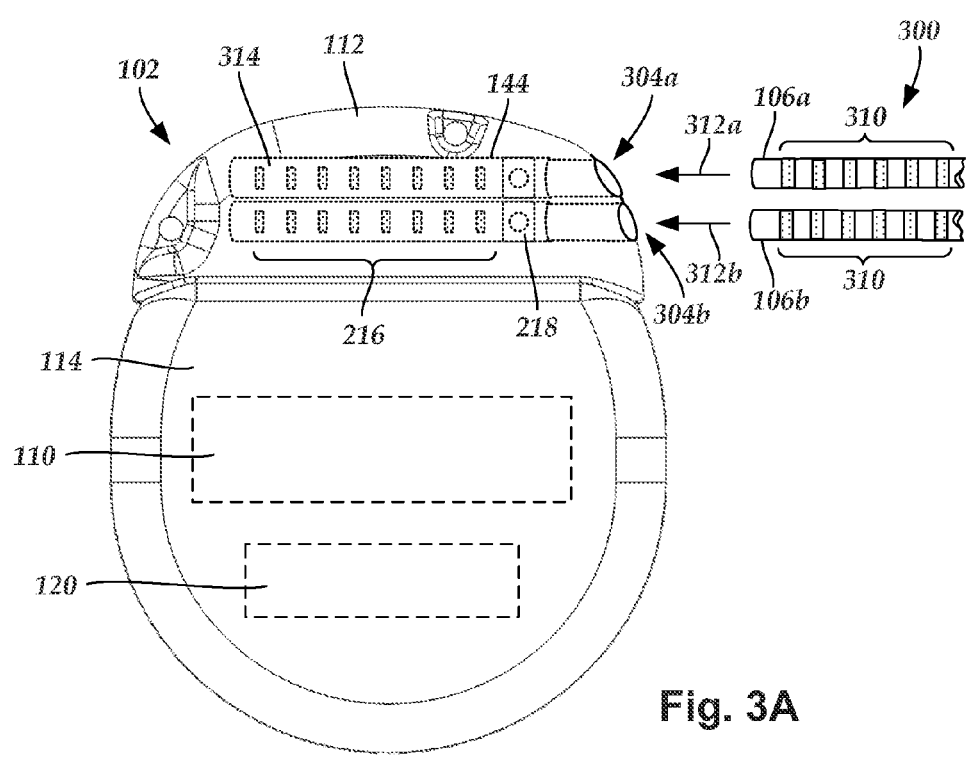
FIG. 3A is a schematic view of one embodiment of the control module of FIG. 1 configured and arranged to electrically couple to an elongated device, according to the invention.

Terminals (e.g., 310 in FIGS. 3A-3B) are typically disposed along the proximal end of the one or more lead bodies 106 of the electrical stimulation system 100 (as well as any splitters, lead extensions, adaptors, or the like) for electrical connection to corresponding connector contacts (e.g., 314 in FIG. 3A). The connector contacts are disposed in connectors (e.g., 144 in FIGS. 1-3B; and 322 FIG. 3B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the one or more lead bodies 106, for example, for inserting a stylet to facilitate placement of the one or more lead bodies 106 within a body of a patient. Additionally, there may be one or more lumens (not shown) that open at, or near, the distal end of the one or more lead bodies 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 3A is a schematic side view of one embodiment of a proximal end of one or more elongated devices 300 configured and arranged for coupling to one embodiment of the control module connector 144. The one or more elongated devices may include, for example, one or more of the lead bodies 106 of FIG. 1, one or more intermediate devices (e.g., a splitter, the lead extension 324 of FIG. 3B, an adaptor, or the like or combinations thereof), or a combination thereof.

The control module connector 144 defines at least one port into which a proximal end of the elongated device 300 can be inserted, as shown by directional arrows 312a and 312b. In FIG. 3A (and in other figures), the connector housing 112 is shown having two ports 304a and 304b. The connector housing 112 can define any suitable number of ports including, for example, one, two, three, four, five, six, seven, eight, or more ports.

The control module connector 144 also includes a plurality of connector contacts, such as connector contact 314, disposed within each port 304a and 304b. When the elongated device 300 is inserted into the ports 304a and 304b, the connector contacts 314 can be aligned with a plurality of terminals 310 disposed along the proximal end(s) of the elongated device(s) 300 to electrically couple the control module 102 to the electrodes (134 of FIG. 1) disposed on the paddle body 104 of the lead 103. Examples of connectors in control modules are found in, for example, U.S. Pat. Nos. 7,244,150 and 8,224,450, which are incorporated by reference.

Figure 3B:
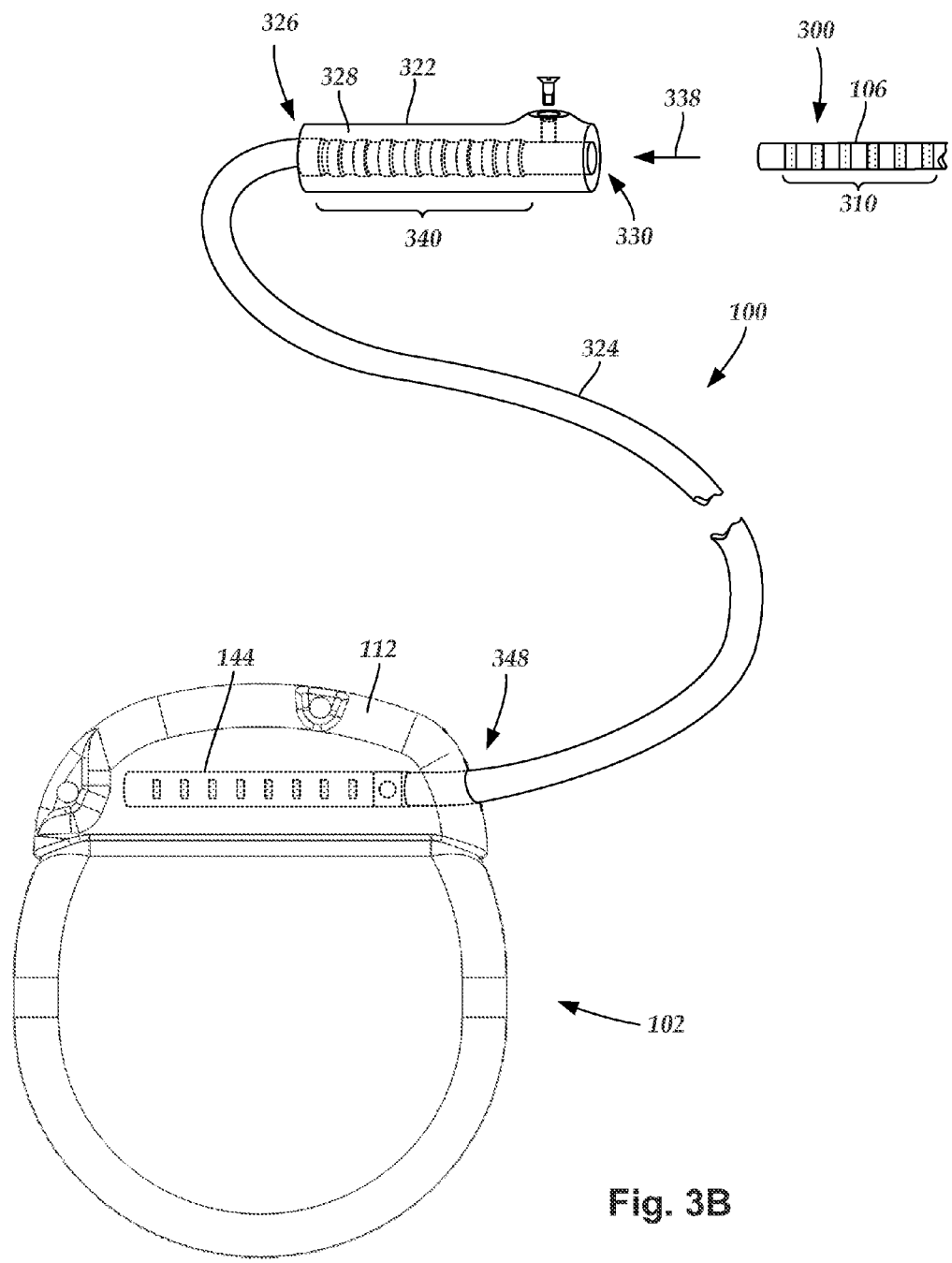
FIG. 3B is a schematic view of one embodiment of a lead extension configured and arranged to electrically couple the elongated device of FIG. 2 to the control module of FIG. 1, according to the invention.

FIG. 3B is a schematic side view of another embodiment of the electrical stimulation system 100. The electrical stimulation system 100 includes a lead extension 324 that is configured and arranged to couple one or more elongated devices 300 (e.g., one of the lead bodies 106 of FIGS. 1 and 2, the splitter 207 of FIG. 2, an adaptor, another lead extension, or the like or combinations thereof) to the control module 102. In FIG. 3B, the lead extension 324 is shown coupled to a single port 304 defined in the control module connector 144. Additionally, the lead extension 324 is shown configured and arranged to couple to a single elongated device 300. In alternate embodiments, the lead extension 324 is configured and arranged to couple to multiple ports 304 defined in the control module connector 144, or to receive multiple elongated devices 300, or both.

A lead extension connector 322 is disposed on the lead extension 324. In FIG. 3B, the lead extension connector 322 is shown disposed at a distal end 326 of the lead extension 324. The lead extension connector 322 includes a connector housing 328. The connector housing 328 defines at least one port 330 into which terminals 310 of the elongated device 300 can be inserted, as shown by directional arrow 338. The connector housing 328 also includes a plurality of connector contacts, such as connector contacts 340. When the elongated device 300 is inserted into the port 330, the connector contacts 340 disposed in the connector housing 328 can be aligned with the terminals 310 of the elongated device 300 to electrically couple the lead extension 324 to the electrodes (134 of FIGS. 1 and 2) disposed along the lead (103 in FIGS. 1 and 2).

In at least some embodiments, the proximal end of the lead extension 324 is similarly configured and arranged as a proximal end of the lead 103 (or other elongated device 300). The lead extension 324 may include a plurality of electrically conductive wires (not shown) that electrically couple the connector contacts 340 to a proximal end 348 of the lead extension 324 that is opposite to the distal end 326. In at least some embodiments, the conductive wires disposed in the lead extension 324 can be electrically coupled to a plurality of terminals (not shown) disposed along the proximal end 348 of the lead extension 324. In at least some embodiments, the proximal end 348 of the lead extension 324 is configured and arranged for insertion into a connector disposed in another lead extension (or another intermediate device). In other embodiments (and as shown in FIG. 3B), the proximal end 348 of the lead extension 324 is configured and arranged for insertion into the control module connector 144.

Figure 4:
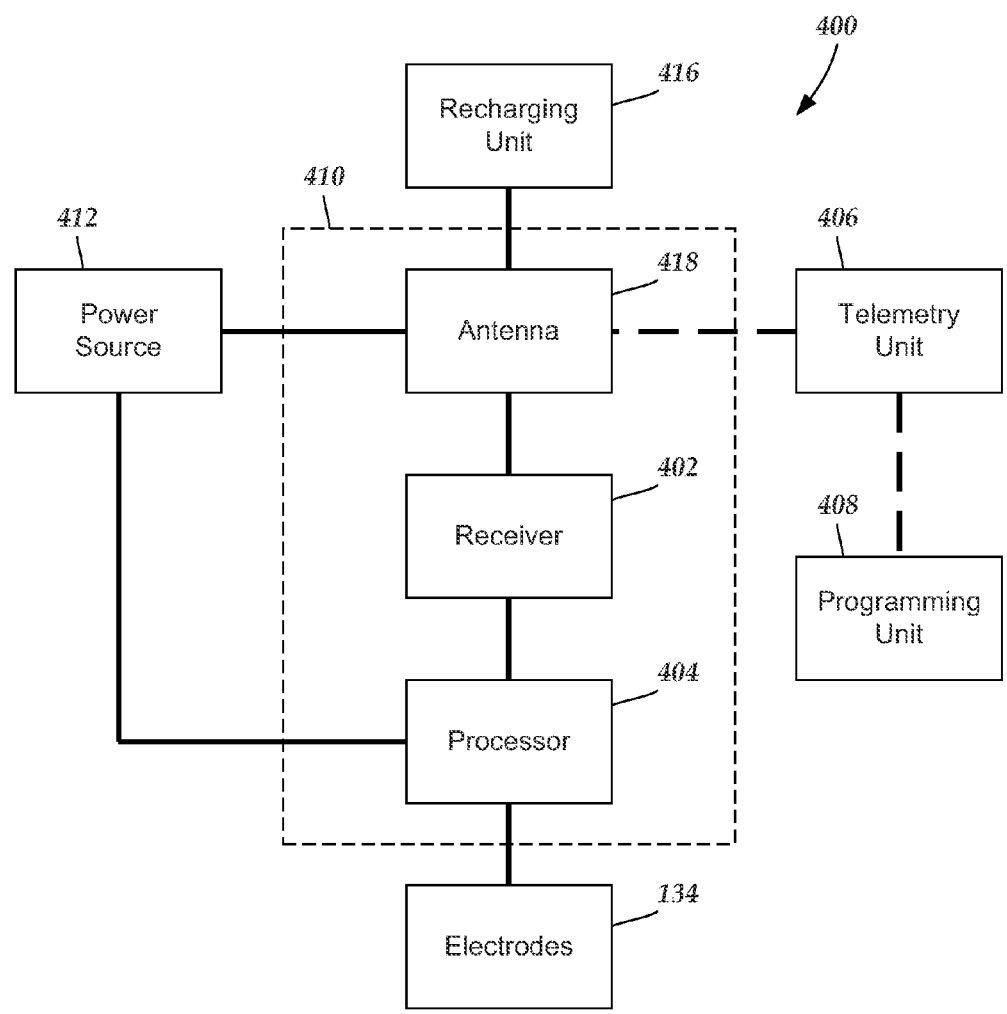
FIG. 4 is a schematic overview of one embodiment of components of a stimulation system, including an electronic subassembly disposed within a control module, according to the invention.

FIG. 4 is a schematic overview of one embodiment of components of an electrical stimulation system 400 including an electronic subassembly 410 disposed within a control module. It will be understood that the electrical stimulation system can include more, fewer, or different components and can have a variety of different configurations including those configurations disclosed in the stimulator references cited herein.

Some of the components (for example, a power source 412, an antenna 418, a receiver 402, and a processor 404) of the electrical stimulation system can be positioned on one or more circuit boards or similar carriers within a sealed housing of an implantable pulse generator or control module, if desired, or within the housing of a microstimulator. Any power source 412 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 418 or a secondary antenna. The external power source can be in a device that is mounted on the skin of the user or in a unit that is provided near the user on a permanent or periodic basis.

If the power source 412 is a rechargeable battery, the battery may be recharged using the optional antenna 418, if desired. Power can be provided to the battery for recharging by inductively coupling the battery through the antenna to a recharging unit 416 external to the user. Examples of such arrangements can be found in the references identified above.

In one embodiment, electrical current is emitted by the electrodes 134 on the paddle or lead body or microstimulator housing to stimulate nerve fibers, muscle fibers, or other body tissues near the electrical stimulation system. The processor 404 is generally included to control the timing and electrical characteristics of the electrical stimulation system. For example, the processor 404 can, if desired, control one or more of the timing, frequency, strength, duration, and waveform of the pulses. In addition, the processor 404 can select which electrodes can be used to provide stimulation, if desired. In some embodiments, the processor 404 selects which electrode(s) are cathodes and which electrode(s) are anodes. In some embodiments, the processor 404 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 408 that, for example, allows modification of pulse characteristics. In the illustrated embodiment, the processor 404 is coupled to a receiver 402 which, in turn, is coupled to the optional antenna 418. This allows the processor 404 to receive instructions from an external source to, for example, direct the pulse characteristics and the selection of electrodes, if desired.

In one embodiment, the antenna 418 is capable of receiving signals (e.g., RF signals) from an external telemetry unit 406 which is programmed by the programming unit 408. The programming unit 408 can be external to, or part of, the telemetry unit 406. The telemetry unit 406 can be a device that is worn on the skin of the user or can be carried by the user and can have a form similar to a pager, cellular phone, or remote control, if desired. As another alternative, the telemetry unit 406 may not be worn or carried by the user but may only be available at a home station or at a clinician's office. The programming unit 408 can be any unit that can provide information to the telemetry unit 406 for transmission to the electrical stimulation system 400. The programming unit 408 can be part of the telemetry unit 406 or can provide signals or information to the telemetry unit 406 via a wireless or wired connection. One example of a suitable programming unit is a computer operated by the user or clinician to send signals to the telemetry unit 406.

The signals sent to the processor 404 via the antenna 418 and the receiver 402 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 400 to cease operation, to start operation, to start charging the battery, or to stop charging the battery. In other embodiments, the stimulation system does not include the antenna 418 or receiver 402 and the processor 404 operates as programmed.

Optionally, the electrical stimulation system 400 may include a transmitter (not shown) coupled to the processor 404 and the antenna 418 for transmitting signals back to the telemetry unit 406 or another unit capable of receiving the signals. For example, the electrical stimulation system 400 may transmit signals indicating whether the electrical stimulation system 400 is operating properly or not or indicating when the battery needs to be charged or the level of charge remaining in the battery. The processor 404 may also be capable of transmitting information about the pulse characteristics so that a user or clinician can determine or verify the characteristics.

Figure 5A:
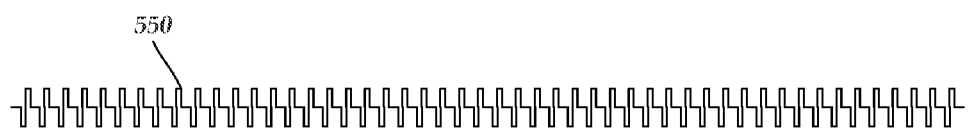
FIG. 5A is a schematic illustration of one embodiment of a series of electrical pulses at a duty cycle of 0%.

The stimulation energy is delivered from the control module 102 to the patient tissue via the lead 103 and its electrodes 134 (or from a microstimulator via electrodes disposed on the housing of the micro stimulator). The stimulation energy is typically delivered as a series of electrical pulses 550, as illustrated in FIG. 5A. The series of electrical pulses is described by stimulation parameters including a stimulation or pulse amplitude and a stimulation or pulse frequency (or a pulse period), as well as the indication of which of the electrodes 134 is to be used for the delivery of stimulation energy. In at least some embodiments, the stimulation or pulse amplitude is in the range of 0 to 25 mA or in the range of 0 to 50 mA. In at least some embodiments, the stimulation or pulse frequency is in the range of 1 to 15000 Hz or in the range of 1 to 2000 Hz or in the range of 1 to 1200 Hz.

One or more of the electrodes can be used as an anode or one or more of the electrodes can be used as a cathode or any combination thereof (e.g., one or more electrodes used as an anode and one or more electrodes used as a cathode). For example, in some embodiments, the stimulation parameters include a single pulse amplitude and single pulse frequency and one or more electrodes specified as anode or cathode.

It will be understood, however, that a more complicated pulsing scheme can be used. For example, the series of electrical pulses may be a combination of two or more subsets of pulses with each subset having stimulation parameters such as, for example, a stimulation amplitude (or pulse amplitude), a stimulation frequency (or pulse frequency or pulse period), and a selection of electrodes as anode or cathode (or any combination of anode and cathode). Other stimulation parameters can include pulse width, pulse shape, or the like. Each subset has a least one of these stimulation parameters that is different from the other subsets. As another example, the subsets of pulses may have different (e.g., alternating) amplitudes or different pulse frequencies or different electrode(s) selected as anode/cathode or any combination thereof or different pulse widths or different pulse shapes, or any combination of these differences. The subsets of pulses can be presented sequentially, simultaneously, overlapping in time, or any combination thereof.

Reduction of the electrical stimulation energy delivered to patient tissue over time can be useful to prolong battery life and, in the case of rechargeable power sources, reduce the frequency or duration (or both) of recharging sessions. Such reduced energy, however, should produce the desired therapeutic effect. Such a reduction can be accomplished, with few or no side effects, by managing the duty cycle of the series of electrical pulses. Side effects can be minimal because the actual interruption or reduction in the series of electrical pulses is relatively brief, as will be described below. The duty cycle is provided to suppress some or all of the pulses from the original amplitude that would have been provided if the duty cycle were not imposed.

A duty cycle parameter can be input into the electrical stimulation system by the user or by a medical practitioner. The duty cycle parameter is an indication of the relative number (for example, percentage) of electrical pulses that are to be suppressed. Suppression can be complete elimination of the suppressed electrical pulses or a reduction in the amplitude of the pulses. The duty cycle parameter can be expressed as a percentage (e.g., an integer in the range of 0 to 100) or as a decimal (e.g., in the range from 0 to 1) or as a fraction or as by any other suitable numerical expression. In the following discussion, the duty cycle parameter will be presented as a percentage, but it will be recognized that any other suitable numerical expression can be used. In some embodiments, any suitable duty cycle within a predetermined range can be selected. In other embodiments, the selection can be limited to two or more choices. For example, the duty cycle parameter may be limited to selection of an integer percentage value or to a percentage value that is a multiple of five or ten. Any suitable limitation on the selection of the duty cycle parameter can be employed.

Figure 5B:
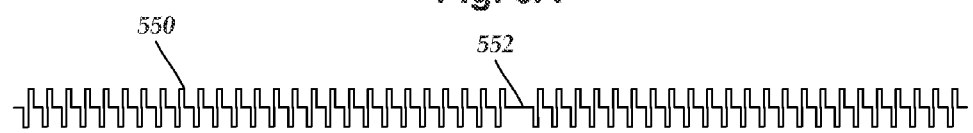
FIG. 5B is a schematic illustration of one embodiment of a series of electrical pulses at a duty cycle of 2% with a uniform distribution, according to the invention.
Figure 5C:
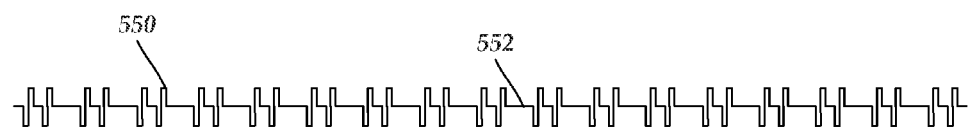
FIG. 5C is a schematic illustration of one embodiment of a series of electrical pulses at a duty cycle of 33% with a uniform distribution, according to the invention.
Figure 5D:
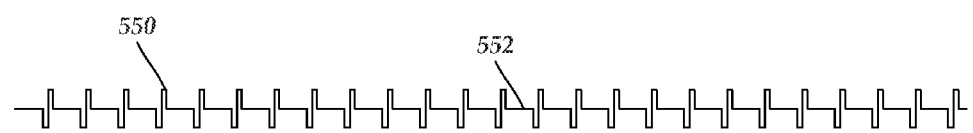
FIG. 5D is a schematic illustration of one embodiment of a series of electrical pulses at a duty cycle of 50% with a uniform distribution, according to the invention.

As an example, a duty cycle parameter of 0% can indicate no suppression of the electrical pulses and a duty cycle parameter of 100% indicates suppression of all of the electrical pulses, as illustrated in FIG. 5A. FIG. 5B illustrates one example of a duty cycle parameter of 2% where two pulses 552 out of every 100 pulses 550 are suppressed. FIGS. 5C illustrates one example of a duty cycle parameter of 33% where one pulse 552 out of every three pulses 550 is suppressed. FIG. 5D illustrates one example of a duty cycle parameter of 50% where one pulse 552 out of every two pulses 550 is suppressed. In some embodiments, the duty cycle parameter is selectable in the range from 0 to 100% (or any other suitable range) optionally in gradations of, for example, 1%, 2%, 5%, or 10% (or any other suitable gradation).

Another parameter, the suppression distribution parameter, can be used to indicate the distribution of suppressed pulses within the series of electrical pulses. FIGS. 5B-5D illustrate a uniform distribution of the suppressed pulses. In such a uniform distribution, the suppressed pulses occur at regular intervals.

Figure 5E:
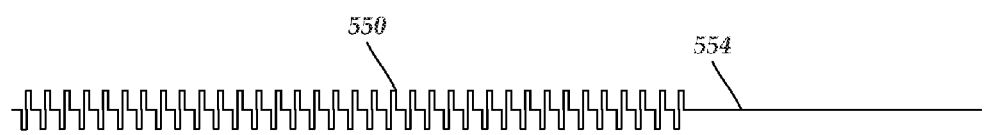
FIG. 5E is a schematic illustration of one embodiment of a series of electrical pulses at a duty cycle of 30% with a consecutive distribution, according to the invention.

The suppressed pulses can also be arranged in a consecutive distribution, as illustrated, for example, in FIG. 5E for a duty cycle parameter of 30% for the electrical pulses 550. In the consecutive distribution, two or more (for example, 2, 3, 4, 5, 8, 10, 12, 16, 20, 25, 30, 33, 50, or more) consecutive pulses 554 are suppressed at regular intervals (for example, every 5, 10, 20, 25, 50, 100, or more pulses). The number of consecutive pulses that are suppressed may be limited by the effect such suppression has on the therapeutic delivery of electrical stimulation. In some embodiments, if the consecutive distribution is selected, the user or practitioner may also select the interval at which the suppressed pulses occur.

Figure 5F:
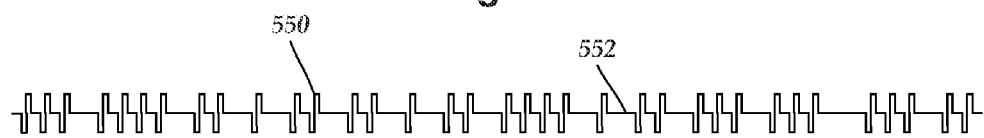
FIG. 5F is a schematic illustration of one embodiment of a series of electrical pulses at a duty cycle of 30% with a random distribution, according to the invention.

The suppressed pulses can also be arranged as a random (including pseudorandom) distribution of suppressed pulses 552 as illustrated, for example, in FIG. 5F. In this example, the duty cycle parameter is 30% for the electrical pulses 550.

Any other suitable distribution of suppressed and unsuppressed pulses can be used. For example, an exponential, arithmetic, or geometric distribution can be employed. One example of an exponential distribution has an arrangement in which one pulse is unsuppressed followed by two suppressed pulses followed by four unsuppressed pulses, followed by eight suppressed pulses, and so on. One example of an arithmetic distribution has an arrangement in which one pulse is unsuppressed followed by two suppressed pulses followed by three unsuppressed pulses, followed by four suppressed pulses, and so on. One example of a geometric distribution has an arrangement in which two pulses are unsuppressed followed by 20 suppressed pulses followed by 200 unsuppressed pulses, and so on. It will be understood that these specific pulse arrangements are merely examples. It will also be understood that any combination of the distributions described herein can also be used.

In some embodiments, the suppression distribution parameter is selectable from at least the following options: uniform distribution, consecutive distribution, and random distribution. In other embodiments, the suppression distribution parameter is selectable from two, three, four, five, or six of the following options: uniform distribution, consecutive distribution, random distribution, exponential distribution, arithmetic distribution, or geometric distribution.

Instead of suppressing the pulses 552, 554 completely (as illustrated in FIGS. 5B-5F), a further parameter can be used; the suppression level parameter. The suppression level parameter is an indication of the reduction of the amplitude of the electrical pulses that are to be suppressed. The suppression level parameter can be expressed as a percentage (e.g., an integer in the range of 0 to 100) or as a decimal (e.g., in the range from 0 to 1) or as a fraction or as by any other expression. In the following discussion, the suppression level parameter will be presented as a percentage, but it will be recognized that any other suitable numerical expression can be used. In some embodiments, any suitable suppression level within a predetermined range can be selected. In other embodiments, the selection can be limited to two or more choices. For example, the suppression level parameter may be limited to selection of an integer percentage value or to a percentage value that is a multiple of five or ten. Any suitable limitation on the selection of the suppression level parameter can be employed.

Figure 5G:
FIG. 5G is a schematic illustration of one embodiment of a series of electrical pulses at a duty cycle of 33% with a uniform distribution and a suppression level of 50%, according to the invention.

For example, a suppression level parameter of 0% can indicate no suppression of electrical pulses. The examples of FIGS. 5B-5F illustrate a suppression level parameter of 100% in which the suppressed electrical pulses are completely eliminated. FIG. 5G illustrates one example of a duty cycle parameter of 33% and a suppression level parameter of 50% with a uniform distribution. In this example, the amplitude of every third electrical pulse is reduced by 50%. In some embodiments, the suppression level parameter is selectable in the range from 0 to 100% optionally in gradations of, for example, 1%, 2%, 5%, or 10%.

A system utilizing the duty cycle parameter can also incorporate either, or both, of the suppression distribution parameter or the suppression level parameter. In some embodiments, any of these three parameters can be altered from an initial or later setting. Selection or alteration of the duty cycle parameter, suppression distribution parameter, or suppression level parameter or any combination thereof may be made by, for example, a practitioner, or any other user, programming the programming unit 408 (FIG. 4) or processor 404 (FIG. 4) or any other processor of the electrical stimulation system. In some embodiments, the patient may be allowed to select or alter any of these parameters.

Figure 6:
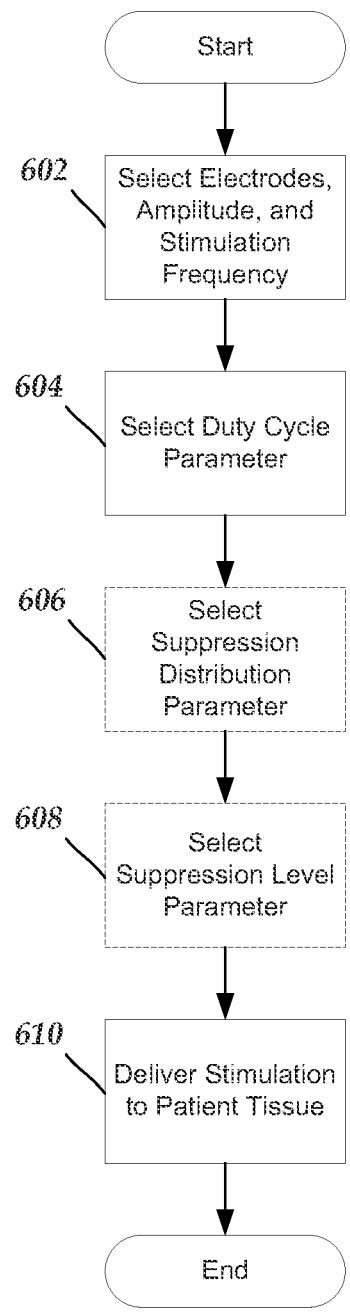
FIG. 6 is a flowchart of one method of delivering electrical stimulation energy using an implantable electrical stimulation system, according to the invention.

FIG. 6 illustrates one example of a method for delivering electrical stimulation to patient tissue. In step 602, stimulation parameters such as electrode selection, stimulation amplitude (or pulse amplitude), stimulation frequency (or pulse frequency or pulse period), pulse width, pulse shape, or any combination thereof can be selected by a practitioner or a patient or any other suitable user. The permission to select any of the parameters described in this paragraph or below may be limited to any subset of the practitioner, patient, or others. For example, in some embodiments, the patient is given permission to set or alter parameters. In other embodiments, the patient is not given permission to set or alter one or more (or even all) of the parameters. It will be understood that other stimulation parameters can be selected and that more complex stimulation patterns may include selection of more than one value for each parameter.

In step 604, a duty cycle parameter is selected by a practitioner or a patient or any other suitable user. The duty cycle parameter is an indication of the relative number of electrical pulses that are to be suppressed.

In optional step 606, a suppression distribution parameter is selected by a practitioner or a patient or other user. The suppression distribution parameter describes the distribution of suppressed pulses within the series of electrical pulses.

In optional step 608, a suppression level parameter is selected by a practitioner or a patient or other user. The suppression level parameter is an indication of the reduction of the amplitude of the electrical pulses that are to be suppressed.

In step 610, electrical stimulation energy is delivered to patient tissue as a series of pulses from the control module through the electrodes of an implanted stimulation lead according to the parameters selected in steps 602 and 604 and optionally steps 606 and 608. It will be recognized that, in at least some embodiments, one or more (or even all) of these selected parameters may be altered during the delivery of electrical stimulation energy.

It will be understood that each block of the flowchart illustration, and combinations of blocks in the flowchart illustration, as well any suitable portion of the electrical stimulation system, external telemetry unit, programming unit, control module, microstimulator, and other systems and methods disclosed herein, can be implemented by computer program instructions. These program instructions may be provided to a processor to produce a machine, such that the instructions, which execute on the processor, create elements for implementing the actions specified in the flowchart block or blocks or described for the external telemetry unit, programming unit, control module, microstimulator, and other systems, and methods disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor (e.g., processors in the external telemetry unit, programming unit, control module, microstimulator, or any combination thereof), such as might arise in a multi-processor computer system. In addition, one or more processes may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks ("DVD") or other optical storage, magnetic cassettes, magnetic tape, magnetic disk storage or other magnetic storage devices, or any other medium, including any non-transitory computer-readable medium, which can be used to store the desired information and which can be accessed by a computing device.

The methods, systems, and devices described herein may be embodied in many different forms and should not be construed as limited to the embodiments set forth herein. Accordingly, the methods, systems, and devices described herein may take the form of an entirely hardware embodiment, an entirely software embodiment or an embodiment combining software and hardware aspects. The systems and devices described herein typically include mass memory and can include communication between devices. The mass memory illustrates a type of computer-readable media, namely computer storage media. Computer storage media may include volatile, nonvolatile, non-transitory, removable, or non-removable media implemented in any method or technology for storage of information, such as computer readable instructions, data structures, program modules, or other data.

Methods of communication between devices or components of a system can include wired or wireless (e.g., RF, optical, or infrared) communications methods or any combination thereof and such methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A non-transitory computer-readable storage medium having processor-executable instructions for delivering electrical stimulation energy through at least one electrode of an implantable electrical stimulation system, the processor-executable instructions when installed onto a system enable the system to perform actions, the processor-executable instructions comprising:
receiving a plurality of stimulation parameters comprising a selection of one or more electrodes, a stimulation amplitude, and a stimulation frequency, wherein the stimulation parameters define, at least in part, an electrical stimulation energy deliverable as a series of electrical pulses at the stimulation frequency;
receiving a duty cycle parameter, wherein the duty cycle parameter indicates a ratio of a number of the electrical pulses to be suppressed to a total number of electrical pulses; and
delivering the electrical stimulation energy to patient tissue through the one or more electrodes, wherein a percentage of the electrical pulses are suppressed according to the duty cycle parameter.

2. The non-transitory computer-readable storage medium of claim 1, wherein the duty cycle parameter is a percentage of the electrical pulses to be suppressed.

3. The non-transitory computer-readable storage medium of claim 1, wherein the processor-executable instructions further comprise receiving a distribution parameter, wherein the distribution parameter indicates how suppressed electrical pulses are be distributed among the electrical pulses.

4. The non-transitory computer-readable storage medium of claim 3, wherein the distribution parameter indicates uniform distribution and wherein delivering the electrical stimulation energy comprises delivering the electrical stimulation energy to patient tissue through the electrical stimulation system, wherein some of the electrical pulses are suppressed according to the duty cycle parameter in a uniform pattern.

5. The non-transitory computer-readable storage medium of claim 3, wherein the distribution parameter indicates random distribution and wherein delivering the electrical stimulation energy comprises delivering the electrical stimulation energy to patient tissue through the electrical stimulation system, wherein some of the electrical pulses are suppressed according to the duty cycle parameter in a random pattern.

6. The non-transitory computer-readable storage medium of claim 3, wherein the distribution parameter indicates consecutive distribution and wherein delivering the electrical stimulation energy comprises delivering the electrical stimulation energy to patient tissue through the electrical stimulation system, wherein some of the electrical pulses are suppressed according to the duty cycle parameter in a periodic interval with at least two consecutive electrical pulses suppressed in each period of the periodic interval.

7. The non-transitory computer-readable storage medium of claim 1, wherein the processor-executable instructions further comprise receiving a suppression level parameter, wherein the suppression level parameter indicates a reduction of the stimulation amplitude for each electrical pulse that is to be suppressed according to the duty cycle parameter.

8. The non-transitory computer-readable storage medium of claim 7, wherein the suppression level parameter is a percentage by which the stimulation amplitude is to be reduced for each electrical pulse that is to be suppressed according to the duty cycle parameter.

9. A method of delivering electrical stimulation energy using an implantable electrical stimulation system, the method comprising:
receiving a plurality of stimulation parameters comprising a selection of one or more electrodes, a stimulation amplitude, and a stimulation frequency, wherein the stimulation parameters define, at least in part, an electrical stimulation energy deliverable as a series of electrical pulses at the stimulation frequency;
receiving a duty cycle parameter, wherein the duty cycle parameter indicates a r ratio of a number of the electrical pulses to be suppressed to a total number of electrical pulses; and
delivering the electrical stimulation energy to patient tissue through the one or more electrodes, wherein a percentage of the electrical pulses are suppressed according to the duty cycle parameter.

10. The method of claim 9, further comprising receiving a distribution parameter, wherein the distribution parameter indicates how suppressed electrical pulses are to be distributed among the electrical pulses.

11. The method of claim 10, wherein the distribution parameter indicates uniform distribution and wherein delivering the electrical stimulation energy comprises delivering the electrical stimulation energy to patient tissue through the electrical stimulation system, wherein some of the electrical pulses are suppressed according to the duty cycle parameter in a uniform pattern.

12. The method of claim 10, wherein the distribution parameter indication random distribution and wherein delivering the electrical stimulation energy comprises delivering the electrical stimulation energy to patient tissue through the electrical stimulation system, wherein some of the electrical pulses are suppressed according to the duty cycle parameter in a random pattern.

13. The method of claim 10, wherein the distribution parameter indicates consecutive distribution and wherein delivering the electrical stimulation energy comprises delivering the electrical stimulation energy to patient tissue through the electrical stimulation system, wherein some of the electrical pulses are suppressed according to the duty cycle parameter in a periodic interval with at least two consecutive electrical pulses suppressed in each period of the periodic interval.

14. The method of claim 9, further comprising receiving a suppression level parameter, wherein the suppression level parameter indicates a reduction of the stimulation amplitude for each electrical pulse that is to be suppressed according to the duty cycle parameter.

15. An electrical stimulation system, comprising:
an electrical stimulation lead comprising a plurality of electrodes;
a control module coupleable to the electrical stimulation lead; and
a processor in communication with the control module, the processor for executing processor-readable instructions that enable actions, comprising:
receiving a plurality of stimulation parameters comprising a selection of one or more of the plurality of electrodes of the stimulation lead, a stimulation amplitude, and a stimulation frequency, wherein the stimulation parameters define, at least in part, an electrical stimulation energy deliverable as a series of electrical pulses at the stimulation frequency;

receiving a duty cycle parameter, wherein the duty cycle parameter indicates a ratio of a number of the electrical pulses to be suppressed to a total number of electrical pulses; and delivering the electrical stimulation energy to patient tissue through the plurality of electrodes of the stimulation lead, wherein a percentage of the electrical pulses are suppressed according to the duty cycle parameter.

16. The electrical stimulation system of claim 15, wherein the actions further comprise receiving a distribution parameter, wherein the distribution parameter indicates how suppressed electrical pulses are be distributed among the electrical pulses.

17. The electrical stimulation system of claim 16, wherein the distribution parameter indicates uniform distribution and wherein delivering the electrical stimulation energy comprises delivering the electrical stimulation energy to patient tissue through the stimulation lead, wherein some of the electrical pulses are suppressed according to the duty cycle parameter in a uniform pattern.

18. The electrical stimulation system of claim 16, wherein the distribution parameter indication random distribution and wherein delivering the electrical stimulation energy comprises delivering the electrical stimulation energy to patient tissue through the stimulation lead, wherein some of the electrical pulses are suppressed according to the duty cycle parameter in a random pattern.

19. The electrical stimulation system of claim 16, wherein the distribution parameter indicates consecutive distribution and wherein delivering the electrical stimulation energy comprises delivering the electrical stimulation energy to patient tissue through the stimulation lead, wherein some of the electrical pulses are suppressed according to the duty cycle parameter in a periodic interval with at least two consecutive electrical pulses suppressed in each period of the periodic interval.

20. The electrical stimulation system of claim 15, wherein the action further comprise receiving a suppression level parameter, wherein the suppression level parameter indicates a reduction of the stimulation amplitude for each electrical pulse that is to be suppressed according to the duty cycle parameter.

* * * * *